(12) United States Patent
Xu

(10) Patent No.: US 9,296,721 B1
(45) Date of Patent: Mar. 29, 2016

(54) METHOD FOR PREPARING ALK INHIBITOR CERITINIB

(71) Applicant: Yong Xu, San Diego, CA (US)

(72) Inventor: Yong Xu, San Diego, CA (US)

( * ) Notice: Subject to any disclaimer, the term of this patent is extended or adjusted under 35 U.S.C. 154(b) by 0 days.

(21) Appl. No.: 14/622,640

(22) Filed: Feb. 13, 2015

(51) Int. Cl.
*C07D 239/48* (2006.01)
*C07D 401/12* (2006.01)
*C07D 211/26* (2006.01)

(52) U.S. Cl.
CPC ............ *C07D 401/12* (2013.01); *C07D 211/26* (2013.01)

(58) Field of Classification Search
CPC .................................................... C07D 239/48
See application file for complete search history.

(56) References Cited

FOREIGN PATENT DOCUMENTS

WO  WO 2008/073687  *  6/2008  ........... C07D 213/74

* cited by examiner

*Primary Examiner* — Erich A Leeser
(74) *Attorney, Agent, or Firm* — Houtteman Law LLC

(57) ABSTRACT

Embodiment of present disclosure provides a method for preparing ceritinib of formula I, comprising: (1) contacting a compound of formula 12b with an amino protective group to obtain a compound of formula 3; (2) contacting the compound of formula 3 with a compound of formula 9a to obtain a compound of formula 5; and (3) subjecting the compound of formula 5 to a deprotection reaction to obtain the ceritinib of formula I. Then ceritinib may be effectively prepared.

14 Claims, No Drawings

METHOD FOR PREPARING ALK INHIBITOR CERITINIB

FIELD

The present disclosure relates to a chemical medicine field, it relates generally to the synthesis of ALK inhibitor ceritinib. Specifically, the disclosure relates to the process for preparation of ceritinib and intermediates thereof.

BACKGROUND

Anaplastic lymphoma kinase (ALK) inhibitors are efficient anti-cancer drugs acting on tumours with affecting anaplastic lymphoma kinase (ALK) such as an EML4-ALK translocation. Ceritinib (trade name Zykadia), an ALK inhibitor in the form of 150 mg of oral capsule, is a drug for the treatment of lung cancer sold by Novartis Pharmaceuticals Corp. It was approved in April 2014 by the Food and Drug Administration. It is indicated for the treatment of patients with ALK-positive metastatic non-small cell lung cancer (NSCLC) who have progressed on or are intolerant to crizotinib. Ceritinib is described chemically as 5-Chloro-N4-[2-[(1methylethyl)sulfonyl]phenyl]-N2-[5-methyl-2-(1-methylethoxy)-4-(4-piperidinyl)phenyl]-2,4-pyrimidinediamine. The molecular formula for ceritinib is C28H36N5O3ClS; the molecular weight is 558.14 g/mole, and has the structural formula shown as Formula I:

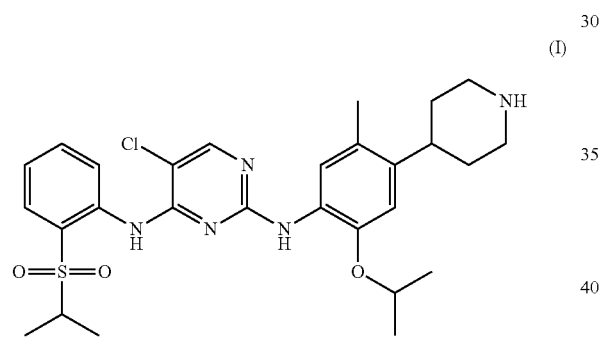

(I)

International patent application Publication No. WO2008/073687 and Journal of Medicinal Chemistry, 2013, 56(14): 5675-5690 (a review) disclose the preparation method of ceritinib and closely related analogues. The method is based on 2-(isopropylsulfonyl)benzenamine (8a) and 2,4,5-trichloropyrimidine as starting materials; it first reacts with 4-bit nucleophilic substitution to get an intermediate 2,5-dichloro-N-(2-(isopropylsulfonyl)phenyl)pyrimidin-4-amine (9a), then the compound and the other intermediate tert-butyl 4-(4-amino-5-isopropoxy-2-methylphenyl)piperidine-1-carboxylate (13b)(it's given from 2-chloro-4-fluoro-1-methylbenzene, as shown below occurs the coupling reaction. Finally, the resultant removes N-protecting group to get ceritinib (Formula I), the synthetic route of ceritinib is shown below.

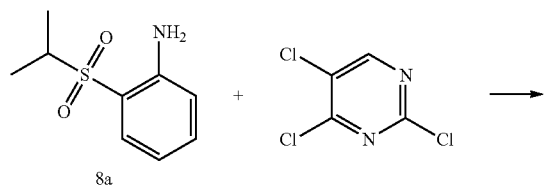

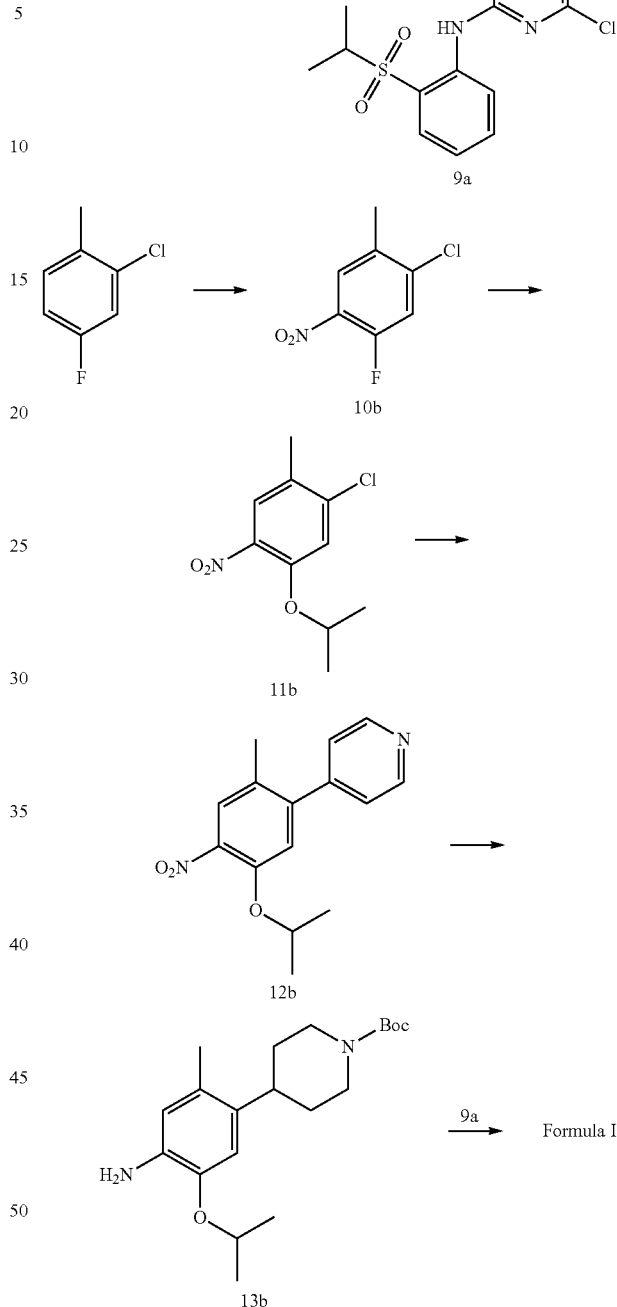

Most of the procedures of the reactions of the above solutions need isolation and purification by column chromatography, which is a tedious operation with low efficiency and is not suitable for industrial amplification. More importantly, in the reduction reaction, compound 12b (4-(5-isopropoxy-2-methyl-4-nitrophenyl)pyridine) is reduced in presence of platinum oxide ($PtO_2$) catalyst to the compound 13b, and the key coupling step uses $Pd(OAc)_2$ as a catalyst. The use of heavy metal in these two reactions results in a greater amount of solid waste, having a great influence on the final product of metal residues.

DESCRIPTION OF THE DISCLOSURE

It is an object of the present disclosure to devise another, improved process for the synthesis of ALK inhibitor ceritinib avoiding the disadvantages of the prior art.

It has now been found, surprisingly, inexpensive, environmentally friendly Lewis acid or organic acid, may be used to improve the coupling reaction of formula I, and the method of present disclosure may avoid the above mentioned disadvantages, and is economically and industrially applicable.

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

According to the present disclosure, it is devised a process of preparing a compound of formula I:

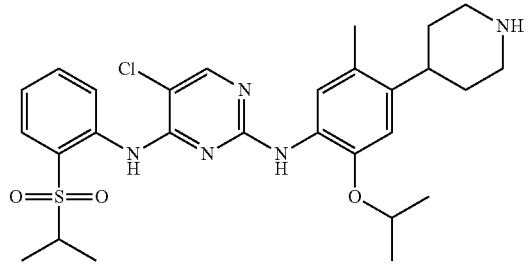

(I)

The technical solutions of the present disclosure include: the compound of formula 3 is prepared by a process comprising reacting a compound of formula 12b with amino-group protective agent, the compound of formula 5 is prepared by a process comprising reacting a compound of formula 3 with a compound 9a, and compound 5 is deprotected (removing the amino protective group (GP)) to finally obtain ceritinib (formula I).

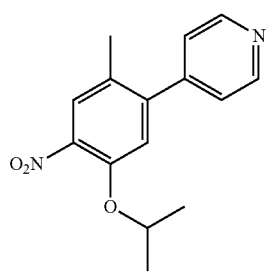

12b

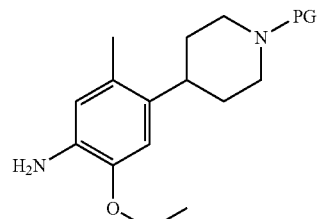

3

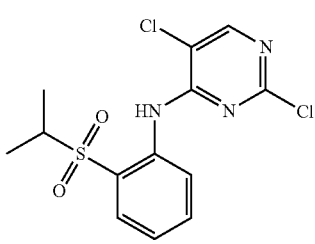

9a

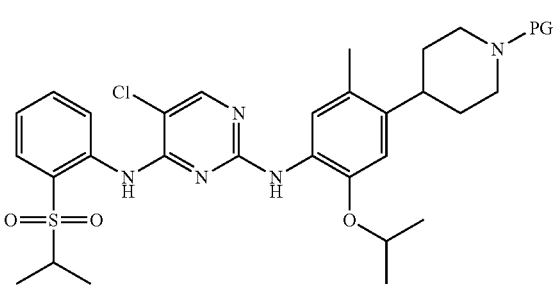

5

(formula I)

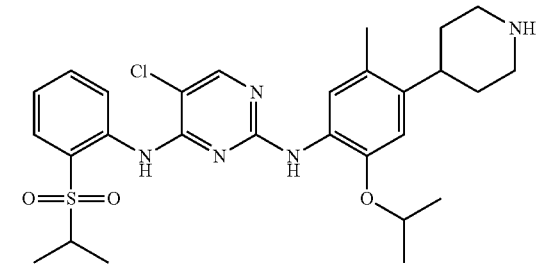

ceritinib

In the above formula 3 and formula 5, PG represents an amino protective group.

Further, according to an embodiment of the present disclosure, the preparation method of ceritinib includes the following steps:

Step (A): amino-protection reaction: reacting a compound of formula 12b and the amino-group protective agent to obtain a compound 3a.

Step (B): coupling reaction: the coupling reaction may take place when compound 3 react with compound 9a to give compound 5, by the Lewis acid or organic acid.

Step (C): deprotection reaction: compound 5 may be subjected to deprotection reaction to finally obtain ceritinib.

According to some embodiments of the present disclosure, in the following examples, the amino-group protective agent may be di-tert-butyl dicarbonate ((BOC)$_2$O) or benzyl chloroformate (CbzCl).

According to some embodiments of the present disclosure, in the following examples, the Lewis acid may be BF$_3$, SbF$_5$ (antimony pentafluoride), AlCl₃ or ZnCl₂. The organic acid may be p-toluenesulfonic acid.

Two preparation methods of ceritinib are described in the following schemes.

In some embodiments, in the method one disclosed herein, the preparation method of the present disclosure is as follows.

Step (A-1): amino-protection reaction: reacting a compound of formula 12b and the amino-group protective agent of (BOC)₂O to obtain a compound 3a (according to some embodiments of present disclosure, the compound 3a may also be prepared according to the method described in J. Med. Chem. 2013, 56, 5675-5690, which is incorporated by reference).

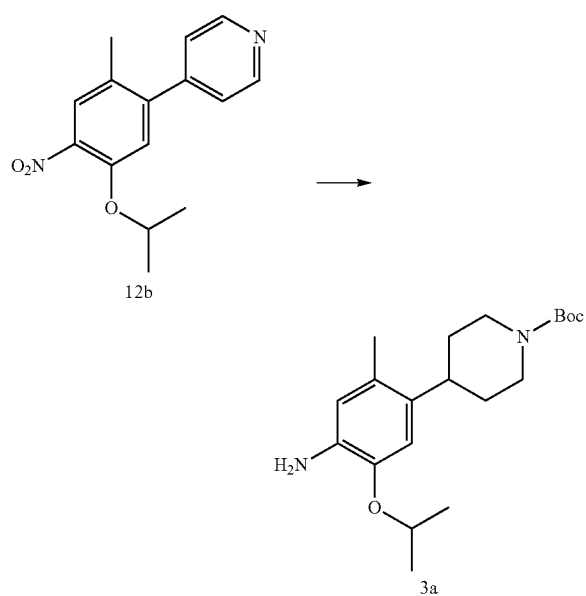

Step (B-1): coupling reaction: the coupling reaction may take place when compound 3 react with compound 9a to give compound 5, and the coupling reaction may be carried out in the presence of a Lewis acid and dimethylcarbinol (IPA).

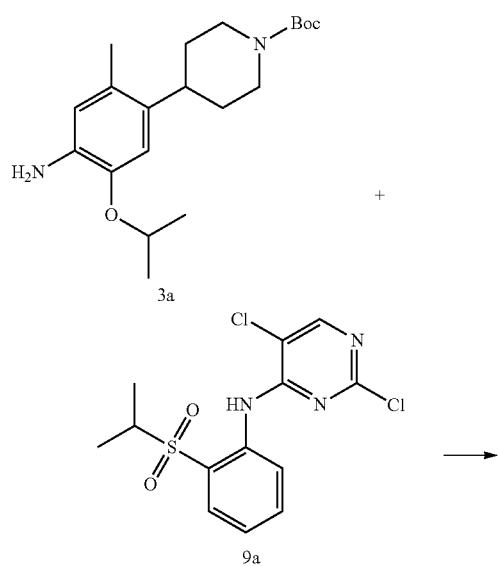

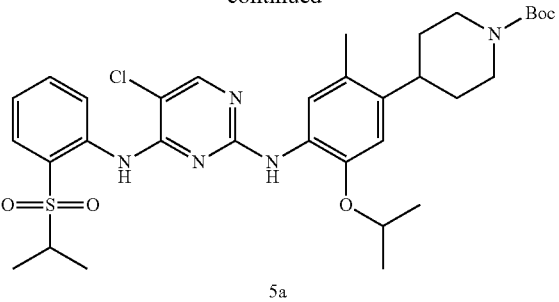

According to some embodiments of the present disclosure, in the method one disclosed herein, a compound of formula 5a may be formed from the compound of formula 3a and formula 9a by means of a coupling reaction, the reaction in step (B-1) is performed at a temperature from 50° C. to 90° C., the step (B-1) reaction system may be stirred and kept for a period of time, in some embodiments, the period of time is from 0.25 hour (15 minutes) to 15 hours. In some embodiments, the formula 9a may be used at an amount of 0.95 equivalent to 1.50 equivalents per 1 equivalent by mole of the formula 3a. The Lewis acid in step (B-1) may be used at an amount of 0.95 equivalent to 1.50 equivalents per 1 equivalent by mole of the formula 3a. The organic solvent used in step (B-1) may be IPA, and the amount of IPA is 2 equivalent to 80 equivalents per 1 equivalent by weight of the formula 3a. Purification step may be involved after completing the reaction of deportation to obtain formula 5a.

According to some embodiments of the present disclosure, in the following examples, the Lewis acid may be BF₃, SbF₅ (antimony pentafluoride), AlCl₃ or ZnCl₂.

According to some embodiments of the present disclosure, in the method one disclosed herein, the reaction in step (B-1) is performed at a temperature from 50° C. to 90° C. In some other embodiments, the reaction in step (B-1) is performed at a temperature from 65° C. to 85° C. In some embodiments, the reaction temperature is from 50° C. to 90° C. In other embodiments, the reaction temperature is from 65° C. to 85° C. In still other embodiments, the reaction temperature is from 70° C. to 80° C. In yet other embodiments, the reaction temperature is 50° C., 55° C., 60° C., 65° C., 70° C., 75° C., 78° C., 80° C., 85° C. or 90° C.

According to some embodiments of the present disclosure, in the method one disclosed herein, the step (B-1) reaction system was stirred and kept for a period of time, in some embodiments, the period of time is from 0.25 hour (15 minutes) to 15 hours. In other embodiments, the period of time is from 1 hour to 10 hours. In other embodiments, the period of time is from 2 hours to 8 hours. In still other embodiments, the period of time is from 3 hours to 6 hours. In yet other embodiments, the period of time is 15 minutes, 1 hour, 1.5 hours, 2 hours, 3 hours, 4 hours, 5 hours, 6 hours, 7 hours, 8 hours, 10 hours, 12 hours or 15 hours.

According to some embodiments of the present disclosure, in the method one disclosed herein, a compound of formula 5a may be formed from the compound of formula 3a and formula 9a by means of a coupling reaction. The formula 9a in step (B-1) may be used at an amount of 0.95 equivalent to 1.50 equivalents per 1 equivalent by mole of the formula 3a. In other embodiments, the amount is 0.98 equivalent to 1.35 equivalents per 1 equivalent by mole of the formula 3a. In other embodiments, the amount is 1.00 equivalent to 1.25 equivalents per 1 equivalent by mole of the formula 3a. In other embodiments, the amount is 1.05 equivalent to 1.15 equivalents per 1 equivalent by mole of the formula 3a. In yet other embodiments, the amount is 0.95, 0.98, 1.00, 1.05, 1.10, 1.15, 1.20, 1.25, 1.30, 1.35, 1.40, or 1.50 equivalents per 1 equivalent by mole of the formula 3a.

According to some embodiments of the present disclosure, in the method one disclosed herein, the Lewis acid in step (B-1) may be used at an amount of 0.95 equivalent to 1.50 equivalents per 1 equivalent by mole of the formula 3a. In other embodiments, the amount is 0.98 equivalent to 1.35 equivalents per 1 equivalent by mole of the formula 3a. In other embodiments, the amount is 1.00 equivalent to 1.25 equivalents per 1 equivalent by mole of the formula 3a. In other embodiments, the amount is 1.05 equivalent to 1.15 equivalents per 1 equivalent by mole of the formula 3a. In yet other embodiments, the amount is 0.95, 0.98, 1.00, 1.05, 1.10, 1.15, 1.20, 1.25, 1.30, 1.35, 1.40, or 1.50 equivalents per 1 equivalent by mole of the formula 3a.

According to some preferred embodiments of the present disclosure, in the method one disclosed herein, the organic solvent used in step (B-1) may be IPA, and the IPA solvent may be used at an amount of 2 equivalent to 80 equivalents per 1 equivalent by weight of the formula 3a. In other embodiments, the amount is 5 equivalent to 50 equivalents per 1 equivalent by weight of the formula 3a. In other embodiments, the amount is 10 equivalent to 30 equivalents per 1 equivalent by weight of the formula 3a. In yet other embodiments, the amount is 2, 3, 5, 8, 10, 18, 20, 24, 30, 40, 50, 60 or 80 equivalents per 1 equivalent by weight of the formula 3a.

According to one embodiment of the present disclosure, the method one disclosed herein, in 2,5-dichloro-N-(2-(isopropylsulfonyl)phenyl)pyrimidin-4-amine (compound of formula 9a, 2.0 g, 5.78 mmol) may be dissolved in isopropanol (60.0 g), then add tert-butyl 4-(4-amino-5-isopropoxy-2-methylphenyl)piperidine-1-carboxylate (compound of formula 3a, 2.0 g, 5.74 mmol) and AlCl₃ (0.786 g, 5.76 mmol). The mixture may be stirred for 6 hours under 80° C., and the reaction may be finished by TLC test. After the reaction, the reaction mixture was concentrated under reduced pressure, the solid residues was dispersed with 200 mL ethyl acetate (EA). The organic layer was washed with saturated aqueous sodium bicarbonate (200 mL), water (100 mL) and saturated aqueous sodium chloride (100 mL), dried over anhydrous sodium sulfate and concentrated to give the compound of formula 5a product as a yellow solid (3.013 g, yield 80.0%).

Step (C-1): deprotection reaction: reacting the compound of formula 5a and trifluoroacetic acid by deprotection reaction to obtain a compound of ceritinib.

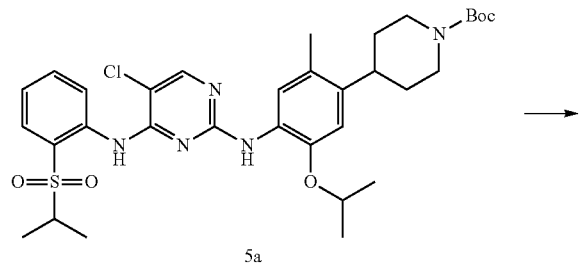

5a

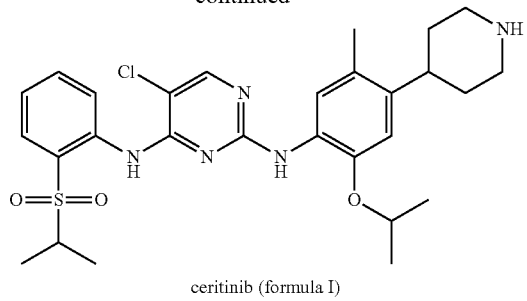

ceritinib (formula I)

According to some embodiments of the present disclosure, in the method one disclosed herein, reacting the compound of formula 5a by dropping trifluoroacetic acid (TFA) slowly in step (C-1), the TFA was slowly added dropwise at a temperature of −15° C. to 15° C. The TFA in step (C-1) is applied in an amount, in some embodiments, the TFA amount is 1.0 equivalent to 2.5 equivalents per 1 equivalent by mole of the formula 5a. The reaction solvent is tetrahydrofuran (THF). The stirring reaction time of formula 5a and trifluoroacetic acid in step (C-1) is kept for a period of time, in some embodiments, the period of time is from 0.5 hour (30 minutes) to 12 hours. The stirring reaction temperature of formula 5a and trifluoroacetic acid in step (C-1) is from 10° C. to 40° C. After complete the reaction, then carry out a purification treatment, thus to give ceritinib product.

According to some embodiments of the present disclosure, in the method one disclosed herein, in some other embodiments, the dropping temperature (namely the temperature under which TFA is added) of TFA is from −15° C. to 15° C. in step (C-1). In some other embodiments, the dropping temperature of TFA is from −10° C. to 10° C. In still other embodiments, the dropping temperature of TFA is from −5° C. to 5° C. In yet other embodiments, the dropping temperature of TFA is −15° C., −10° C., −5° C., 0° C., 5° C., 8° C., 10° C. or 15° C.

According to some embodiments of the present disclosure, in the method one disclosed herein, ceritinib may be formed from the compound of formula 5a and TFA by means of a deprotection reaction. TFA in step (C-1) may be used at an amount of 1.0 equivalent to 2.5 equivalents per 1 equivalent by mole of the formula 5a. In other embodiments, the amount is 1.05 equivalent to 2.0 equivalents per 1 equivalent by mole of the formula 5a. In other embodiments, the amount is 1.1 equivalent to 1.5 equivalents per 1 equivalent by mole of the formula 5a. In yet other embodiments, the amount is 1.0, 1.05, 1.1, 1.2, 1.3, 1.5, 1.8, 2.0 or 2.5 equivalents per 1 equivalent by mole of the formula 5a.

According to some embodiments of the present disclosure, in the method one disclosed herein, in some other embodiments, the stirring reaction temperature of formula 5a and trifluoroacetic acid in step (C-1) is from 10° C. to 40° C. In some other embodiments, the stirring reaction temperature is from 15° C. to 30° C. In still other embodiments, the stirring reaction temperature is from 20° C. to 25° C. In yet other embodiments, the stirring reaction temperature is 10° C., 15° C., 20° C., 22° C., 25° C., 30° C. or 40° C.

According to some embodiments of the present disclosure, in the method one disclosed herein, in some other embodiments, the stirring reaction time of formula 5a and trifluoroacetic acid in step (C-1) is kept for a period of time, in some embodiments, the period of time is from 0.5 hour (30 minutes) to 12 hours. In other embodiments, the period of time is from 1 hour to 10 hours. In other embodiments, the period of time is from 2 hours to 8 hours. In still other embodiments, the period of time is from 3 hours to 6 hours. In yet other embodiments, the period of time is 30 minutes, 1 hour, 2 hours, 3 hours, 4 hours, 5 hours, 6 hours, 8 hours, 10 hours or 12 hours.

According to one embodiment of the present disclosure, in the method one disclosed herein, to a flask were added compound of formula 5a (200 g, 0.305 mol) and THF (1000 mL). The mixture was controlled at 0° C. to 5° C. when TFA (70 g, 0.61 mol) was slowly added. After the TFA dropwise addition, the mixture was kept at 20° C. to 25° C. and stirred for 6 hours. After the reaction, the reaction mixture was concentrated, then was quenched with saturated aqueous sodium bicarbonate (2000 mL) and separated with dichloromethane ($CH_2Cl_2$) (500 mL×3). The organic layer was washed with saturated aqueous sodium bicarbonate (1000 mL), and water (500 mL) and saturated aqueous sodium chloride (500 mL), dried over anhydrous sodium sulfate and filtered, and concentrated to obtain the raw product of ceritinib. To the raw product was added i-propanol (IPA) (480 mL). The mixture was heated until dissolved completely, cooled to 30° C., and then kept at 30° C., stirred and crystallized for 3 hours. The resulting mixture was filtered. The filter cake was dried in vacuo at 60° C. for 8 hours to obtain the ceritinib product (compound of formula I) as a white solid (149.9 g, 88.5%), HPLC purity: 99.2%.

In other embodiments, in the method two disclosed herein, the preparation method of the present disclosure is as follow.

Step (A-2): amino-protection reaction: reacting a compound of formula 12b and the amino-group protective agent of benzyl chloroformate to obtain a compound 3b.

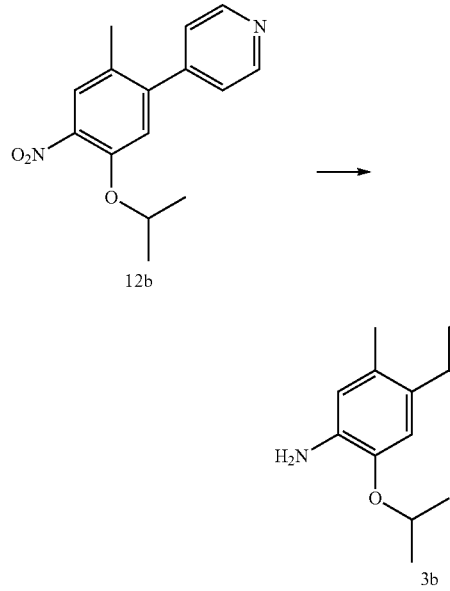

12b

3b

Step (A-2): amino-protection reaction: reacting a compound of formula 12b and the amino-group protective agent of benzyl chloroformate (CbzCl) to obtain a compound 3b.

According to some embodiments of the present disclosure, compound 13 was prepared according to the following method: 4-(5-isopropoxy-2-methyl-4-nitrophenyl)pyridine (compound 12b) (438 mg, 1.61 mmol) dissolved in acetic acid (30 mL) was treated with TFA (0.24 mL, 3.22 mmol) and $PtO_2$ (176 mg, 40% w/w). The reaction mixture was vigorously stirred under 1 atm of $H_2$ for 36 h. The reaction mixture was filtered, and the filtrate was concentrated under vacuum. The resulting residue was diluted with ethyl acetate and washed twice with 1 N aqueous NaOH. The organic layer was then dried over $Na_2SO_4$ and filtered. After concentration, the raw product (391 mg) was dissolved in anhydrous THF (50 mL), triethylamine was added (10 mL) followed. Then slowly added benzyl carbonochloridate (536 mg), controlled at 0° C. to 5° C. at the same time. The mixture was stirred at room temperature for 3 hours, and separated with $CH_2Cl_2$ (50 mL×3). The organic layer was washed with saturated aqueous sodium bicarbonate (100 mL), and water (50 mL) and saturated aqueous sodium chloride (50 mL), dried over anhydrous sodium sulfate and filtered, and concentrated to obtain compound 3b.

Step (B-2): coupling reaction: the coupling reaction was taken place when compound 3 react with compound 9a to give compound 5, wherein the coupling reaction may be carried out in the presence of the organic acid and IPA.

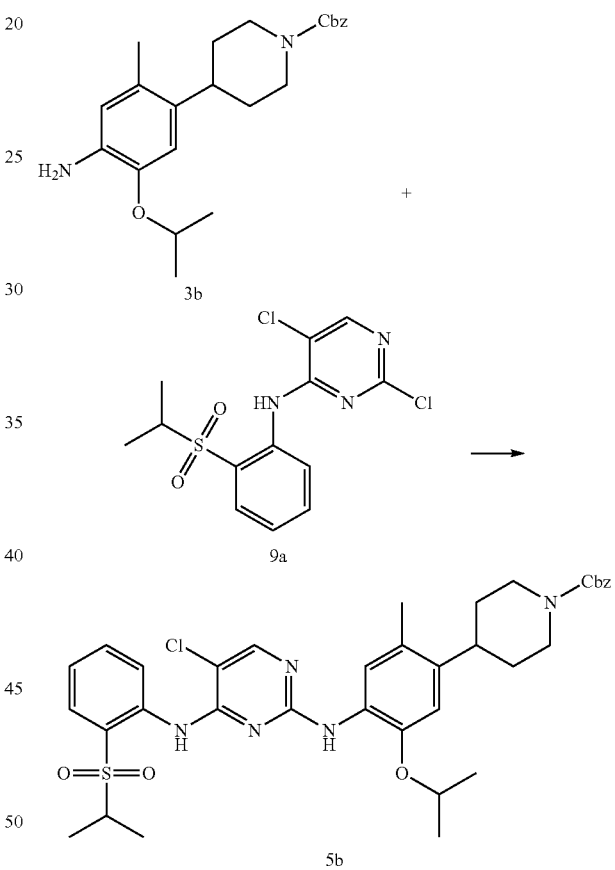

According to some embodiments of the present disclosure, in the following examples, the organic acid may be p-toluenesulfonic acid.

According to some embodiments of the present disclosure, in the method two disclosed herein, a compound of formula 5b may be formed from the compound of formula 3b and formula 9a by means of a coupling reaction, the reaction in step (B-2) is performed at a temperature from 50° C. to 90° C., the step (B-2) reaction was stirred and kept for a period of time, in some embodiments, the period of time is from 0.25 hour (15 minutes) to 15 hours. The formula 9a in step (B-2) may be used at an amount of 0.95 equivalent to 1.50 equivalents per 1 equivalent by mole of the formula 3b. The organic solvent used in step (B-2) is IPA at an amount of 2 equivalent to 80 equivalents per 1 equivalent by weight of the formula 3b. After complete the reaction, then carry out a purification treatment, to give formula 5b.

According to some embodiments of the present disclosure, in the method two disclosed herein, the reaction in step (B-2) is performed at a temperature from 50° C. to 90° C. In some other embodiments, the reaction in step (B-2) is performed at a temperature from 65° C. to 85° C. In some embodiments, the reaction temperature is from 50° C. to 90° C. In other embodiments, the reaction temperature is from 65° C. to 85° C. In still other embodiments, the reaction temperature is from 70° C. to 80° C. In yet other embodiments, the reaction temperature is 50° C., 55° C., 60° C., 65° C., 70° C., 75° C., 78° C., 80° C., 85° C. or 90° C.

According to some embodiments of the present disclosure, in the method two disclosed herein, the step (B-2) reaction was stirred and kept for a period of time, in some embodiments, the period of time is from 0.25 hour (15 minutes) to 15 hours. In other embodiments, the period of time is from 1 hour to 10 hours. In other embodiments, the period of time is from 2 hours to 8 hours. In still other embodiments, the period of time is from 3 hours to 6 hours. In yet other embodiments, the period of time is 15 minutes, 1 hour, 1.5 hours, 2 hours, 3 hours, 4 hours, 5 hours, 6 hours, 7 hours, 8 hours, 10 hours, 12 hours or 15 hours.

According to some embodiments of the present disclosure, in the method two disclosed herein, a compound of formula 5b may be formed from the compound of formula 3b and formula 9a by means of a coupling reaction. The formula 9a in step (B-2) may be used at an amount of 0.95 equivalent to 1.50 equivalents per 1 equivalent by mole of the formula 3b. In other embodiments, the amount is 0.98 equivalent to 1.35 equivalents per 1 equivalent by mole of the formula 3b. In other embodiments, the amount is 1.00 equivalent to 1.25 equivalents per 1 equivalent by mole of the formula 3b. In other embodiments, the amount is 1.05 equivalent to 1.15 equivalents per 1 equivalent by mole of the formula 3b. In yet other embodiments, the amount is 0.95, 0.98, 1.00, 1.05, 1.10, 1.15, 1.20, 1.25, 1.30, 1.35, 1.40, or 1.50 equivalents per 1 equivalent by mole of the formula 3b.

According to one embodiment of the present disclosure, in the method two disclosed herein, the organic solvent used in step (B-2) is IPA, and the IPA solvent may be used at an amount of 2 equivalent to 80 equivalents per 1 equivalent by weight of the formula 3b. In other embodiments, the amount is 5 equivalent to 50 equivalents per 1 equivalent by weight of the formula 3b. In other embodiments, the amount is 10 equivalent to 30 equivalents per 1 equivalent by weight of the formula 3b. In yet other embodiments, the amount is 2, 3, 5, 8, 10, 18, 20, 24, 30, 40, 50, 60 or 80 equivalents per 1 equivalent by weight of the formula 3b.

According to some embodiments of the present disclosure, in the method two disclosed herein, 2,5-dichloro-N-(2-(isopropylsulfonyl)phenyl)pyrimidin-4-amine (compound of formula 9a, 2.0 g, 5.78 mmol) was dissolved in isopropanol (60.0 g), then added benzyl 4-(4-amino-5-isopropoxy-2-methylphenyl)piperidine-1-carboxylate (compound of formula 3b, 2.21 g, 5.78 mmol) and p-toluenesulfonic acid (0.995 g, 5.78 mmol). The mixture was stirred for 5 hours under 75° C., the reaction was finished by TLC test. After the reaction, the reaction mixture was concentrated under reduced pressure, the solid residues was dispersed with 200 mL ethyl acetate (EA). The organic layer was washed with saturated aqueous sodium bicarbonate (200 mL), water (100 mL) and saturated aqueous sodium chloride (100 mL), dried over anhydrous sodium sulfate and concentrated to give the compound of formula 5b product as a yellow powder (3.47 g, yield 86.6%).

Step (C-2): deprotection reaction: reacting the compound of formula 5a, palladium on carbon (Pd/C) and ammonium formate in the $C_{1-4}$ alcohol solvent by deprotection reaction to obtain a compound of ceritinib.

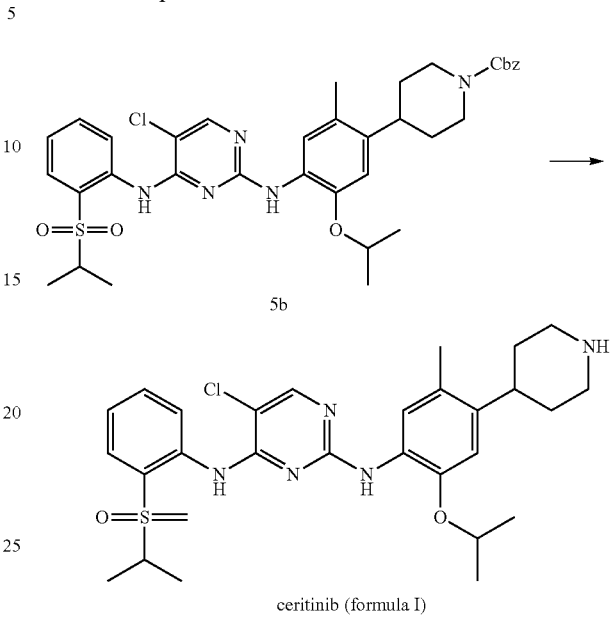

ceritinib (formula I)

According to some embodiments of the present disclosure, in the method two disclosed herein, in some embodiments, the $C_{1-4}$ alcohol for forming ceritinib in the deprotection in step (C-2) may be methanol, ethanol, propanol, i-propanol, n-butanol, i-butanol, or tert-butanol.

According to some embodiments of the present disclosure, in the method two disclosed herein, ammonium formate in step (C-2) is applied in an amount, in some embodiments, the ammonium formate amount is 0.95 equivalent to 1.50 equivalents per 1 equivalent by mole of the formula 5b. The stirring reaction time for forming ceritinib in step (C-2) is kept for a period of time, in some embodiments, the period of time is from 0.5 hour (30 minutes) to 6 hours. The stirring reaction temperature is from 15° C. to 35° C. After complete the reaction, then carry out a purification treatment, to obtain ceritinib.

According to some embodiments of the present disclosure, in the method two disclosed herein, ammonium formate in step (C-2) is applied in an amount, in some embodiments, the ammonium formate amount is 0.95 equivalent to 1.50 equivalents per 1 equivalent by mole of the formula 5b. In other embodiments, the amount is 0.98 equivalent to 1.20 equivalents per 1 equivalent by mole of the formula 5b. In other embodiments, the amount is 1.00 equivalent to 1.10 equivalents per 1 equivalent by mole of the formula 5b. In yet other embodiments, the amount is 0.95, 0.98, 1.00, 1.05, 1.10, 1.20, or 1.50 equivalents per 1 equivalent by mole of the formula 5b.

According to some embodiments of the present disclosure, in the method two disclosed herein, in some other embodiments, the stirring reaction temperature for forming ceritinib in step (C-2) is from 15° C. to 35° C. In some other embodiments, the stirring reaction temperature is from 25° C. to 35° C. In yet other embodiments, the stirring reaction temperature is 15° C., 20° C., 25° C., 30° C. or 35° C.

According to some embodiments of the present disclosure, in the method two disclosed herein, in some other embodiments, the stirring reaction time for forming ceritinib in step (C-2) is kept for a period of time, in some embodiments, the period of time is from 0.5 hour (30 minutes) to 6 hours. In other embodiments, the period of time is from 1 hour to 4 hours. In other embodiments, the period of time is from 2 hours to 3 hours. In yet other embodiments, the period of time is 30 minutes, 1 hour, 2 hours, 2.5 hours, 3 hours, 4 hours, 5 hours or 6 hours.

According to one embodiment of the present disclosure, in the method two disclosed herein, to a flask were added compound of formula 5b (200 g, 0.289 mol) and THF (1000 mL). The mixture was controlled at 0° C. to 5° C. when TFA (51.3 g, 0.45 mol) was slowly added. After the TFA dropwise addition, the mixture was kept at 20° C. to 25° C. and stirred for 5 hours. After the reaction, the reaction mixture was concentrated, then was quenched with saturated aqueous sodium bicarbonate (2000 mL) and separated with dichloromethane ($CH_2Cl_2$) (500 mL×3). The organic layer was washed with saturated aqueous sodium bicarbonate (1000 mL), and water (500 mL) and saturated aqueous sodium chloride (500 mL), dried over anhydrous sodium sulfate and filtered, and concentrated to obtain the raw product of ceritinib. To the raw product was added i-propanol (IPA) (480 mL). The mixture was heated until dissolved completely, cooled to 30° C., and then kept at 30° C., stirred and crystallized for 4 hours. The resulting mixture was filtered. The filter cake was dried in vacuo at 60° C. for 8 hours to obtain ceritinib as a white powder (145.1 g, 90.0%), HPLC purity: 99.5%.

In the present disclosure, the term "comprise" is an open expression, it means comprising the contents disclosed herein, but don't exclude other contents.

The solvent used for the recrystallization of ceritinib in the present disclosure is not particularly restricted, any solvent is contained in the disclosure so long as it can dissolve the raw product and the crystal product can precipitate out under certain conditions. Additionally, many similar modifications in the art, substitutions to same object, or solvent, solvent composition and the solvent composition with different proportions which are equivalent to those described in the disclosure, all are deemed to be included in the present disclosure. Wherein the solvent could be methanol, ethanol, n-propanol, i-propanol, n-butanol, i-butanol, a ethanol-water mixture at a volume ratio 50:50, or a combination thereof.

The amount of water in the solvent is not particularly restricted. So long as the solvent containing a certain amount of water may be used in the reaction disclosed herein, which is deemed to be included in the present disclosure. The amount of water in the solvent is approximately less than 0.05%, less than 0.1%, less than 0.2%, less than 0.5%, less than 5%, less than 10%, less than 25%, less than 30%, or 0%.

Any temperature is included in the present disclosure so long as it can be applicable for the crystallization process of recrystallization. Additionally, many similar modifications in the art, substitutions to same object, or temperature and temperature scope which are equivalent to those described in the disclosure, all are deemed to be included in the present disclosure. In some embodiments, the crystallization temperature is from approximately −80° C. to 60° C. After all the raw product is dissolved completely, the crystallization is at a higher temperature, may be from solvent boiling point to 60° C., from solvent boiling point to 50° C., from solvent boiling point to 40° C., from solvent boiling point to 30° C., from solvent boiling point to 25° C., from solvent boiling point to 0° C., from solvent boiling point to −10° C., from solvent boiling point to −15° C., from solvent boiling point to −20° C., from solvent boiling point to −30° C., from solvent boiling point to −40° C., from solvent boiling point to −50° C., or solvent boiling point to −80° C., and may be from approximately 60° C. to −20° C., from approximately 50° C. to −20° C., from approximately 40° C. to 10° C., from approximately 30° C. to 10° C., or from approximately room temperature (usually 25° C.) to 10° C. The crystallization at the later stage is at a lower temperature, may be from approximately −80° C. to approximately 10° C., from approximately −60° C. to approximately 10° C., from approximately −40° C. to approximately 10° C., from approximately −20° C. to approximately 10° C., from approximately −10° C. to approximately 10° C., from approximately 0° C. to approximately 10° C.

After the reaction proceeds to a certain extent in the present disclosure, such as the raw material is consumed more than 20%, more than 30%, more than 40%, more than 50%, more than 70%, more than 80%, more than 90%, more than 95%, or completely by monitoring, the reaction mixture is worked up, such as cooled, collected, drawn, filtered, separated, purified or a combination thereof. The reaction may be monitored by conventional method such as thin-layer chromatography (TLC), high performance liquid chromatography (HPLC), gas chromatography (GC), and the like. The reaction mixture may be worked up by conventional method, for example, the raw product may be collected by concentrating the reaction mixture through vacuum evaporation or conventional distillation and used directly in the next operation; or the raw product may be obtained by filtration of the reaction mixture and used directly in the next operation; or the raw product may be get by pouring out the supernatant liquid of the reaction mixture after standing a while and used directly in the next operation; and the reaction mixture may be purified by suitable methods such as extraction, distillation, crystallization, column chromatography, washing, trituration with suitable organic solvents or a combination thereof.

The present disclosure improves process for the synthesis of ALK inhibitor ceritinib avoiding the disadvantages of the prior art, these two methods have advantages of convenient work-up, and high yield. In the present disclosure, we use inexpensive, environmentally and friendly Lewis acid or organic acid to improve the coupling reaction and finally easier to get ceritinib. The new preparing method of ceritinib is easier to separate, easier to be controlled and industrialized, and is economical and easier to prepare ceritinib with high purity. In addition, the process of the disclosure possesses the advantages of cheap raw material, mild reaction conditions, simplified operational procedure, safety and controllable, and easy industrialization.

EXAMPLES

The preparation methods of ALK inhibitor ceritinib are disclosed in the examples of the present disclosure. Those skilled in the art can learn from this article to properly improve the process parameters to implement the preparation method. It's to note that all the similar replacements and changes are obvious for the skilled person and within the scope of the present disclosure. The methods disclosed herein are described in the preferred examples. Related persons can clearly realize and apply the techniques disclosed herein by making some changes, appropriate alterations, or combinations to the methods without departing from spirit, principles, and scope of the present disclosure.

In order to further understand the disclosure, it is detailed below through examples.

Example

Example 1

Method one

Preparation of tert-butyl 4-(4-(5-chloro-4-(2-(isopropyl-methylenesulfinyl)phenylamino)pyrimidin-2-ylamino)-5-isopropoxy-2-methylphenyl) piperidine-1-carboxylate (compound of formula 5a)

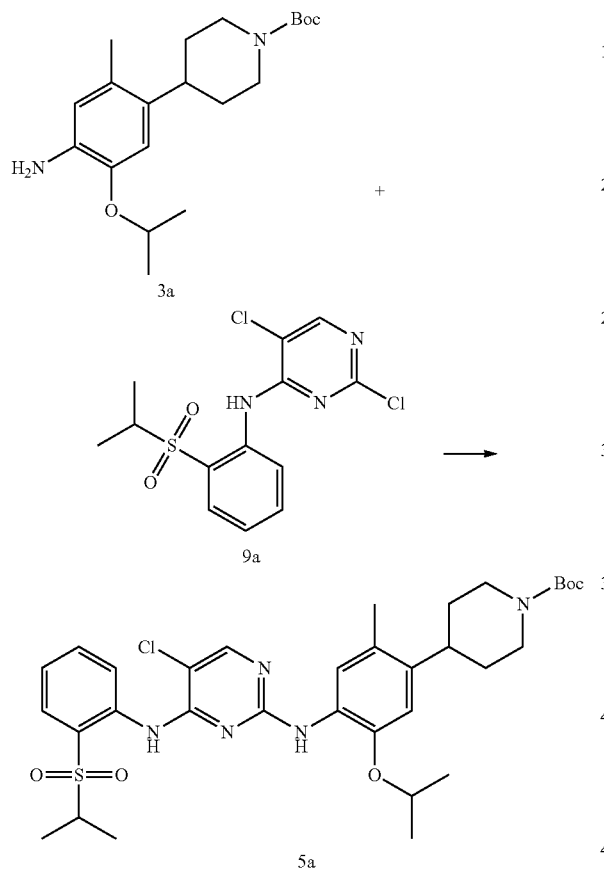

2,5-dichloro-N-(2-(isopropylsulfonyl)phenyl)pyrimidin-4-amine (compound of formula 9a, 2.0 g, 5.78 mmol) was dissolved in isopropanol (60.0 g), then added tert-butyl 4-(4-amino-5-isopropoxy-2-methylphenyl)piperidine-1-carboxylate (compound of formula 3a, 2.0 g, 5.74 mmol) and $AlCl_3$ (0.786 g, 5.76 mmol). The mixture was stirred for 6 hours under 80° C. And the reaction was finished by TLC test. After the reaction, the reaction mixture was concentrated under reduced pressure, the solid residues was dispersed with 200 mL ethyl acetate (EA). The organic layer was washed with saturated aqueous sodium bicarbonate (200 mL), water (100 mL) and saturated aqueous sodium chloride (100 mL), dried over anhydrous sodium sulfate and concentrated to give the compound of formula 5a product as a yellow solid (3.013 g, yield 80.0%).

Example 2

Preparation of Compound 5a

Method One

The compound 5a may be prepared under the reaction conditions shown in table 1 according to the procedure described in Example 1. Among these example numbers, number 1 to number 13 are independently represent for the present disclosure's examples, number 14 to number 16 are independently represent for the comparative examples. From the quality and yield (%) data in table 1, the comparative examples number 14 to number 16 were significantly less than number 1 to number 13 of the present disclosure for compound 5a's product.

According to some embodiments of the present disclosure, in the method disclosed herein, the organic solvent used in step (B-1) is preferred IPA.

TABLE 1

The reaction conditions for preparation of compound 5a

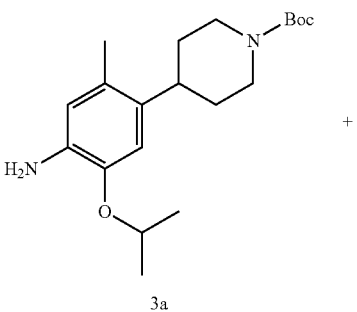 [SMILES: Cc1cc(N)c(OC(C)C)cc1C1CCN(C(=O)OC(C)(C)C)CC1]

TABLE 1-continued

The reaction conditions for preparation of compound 5a

|  | No. | | | | | | | |
| --- | --- | --- | --- | --- | --- | --- | --- | --- |
|  | 1 | 2 | 3 | 4 | 5 | 6 | 7 | 8 |
| The mole ratio of (3a):(9a):(31); (the amount of compound 3a is 2.0 g) | 1/0.95/0.98 | 1/0.98/1.4 | 1/1.10/1.35 | 1/1.0/1.3 | 1/1.05/1.25 | 1/1.15/1.2 | 1/1.2/1.15 | 1/1.25/1.1 |
| Lewis acid(31) | $BF_3$ | $SbF_5$ | $AlCl_3$ | $ZnCl_2$ | $BF_3$ | $SbF_5$ | $AlCl_3$ | $ZnCl_2$ |
| Reaction organic solvent(32) | IPA | IPA | IPA | IPA | IPA | IPA | IPA | IPA |
| The mass ratio of reaction solvent to compound 3a | 2 | 3 | 4 | 8 | 10 | 18 | 20 | 24 |
| Reaction temperature(° C.) | 90 | 85 | 80 | 85 | 75 | 75 | 85 | 78 |
| Reaction time(h) | 0.25 | 1 | 1.5 | 2 | 3 | 4 | 5 | 6 |
| Quality; yield(%) of product | 2.994 g; 79.5 | 2.945 g; 78.2 | 2.983 g; 79.2 | 3.017 g; 80.1 | 3.069 g; 81.5 | 2.945 g; 78.2 | 2.979 g; 79.1 | 3.021 g; 80.2 |
|  | No. | | | | | | | |
|  | 9 | 10 | 11 | 12 | 13 | 14 | 15 | 16 |
| The mole ratio of (3a):(9a):(31); (the amount of compound 3a is 2.0 g) | 1/1.3/1.05 | 1/1.35/1.0 | 1/1.4/0.98 | 1/1.5/0.95 | 1/0.95/1.5 | 1/1.05/1.2 | 1/1/1.1 | 1/1.1/1.0 |
| Lewis acid(31) | $AlCl_3$ | $SbF_5$ | $BF_3$ | $ZnCl_2$ | $BF_3$ | $SbF_5$ | $AlCl_3$ | $ZnCl_2$ |
| Reaction organic solvent(32) | IPA | IPA | IPA | IPA | IPA | ethanol | t-butanol | ethanol and water(v/v = 50:50) |
| The mass ratio of reaction solvent to compound 3a | 30 | 40 | 50 | 60 | 80 | 30 | 30 | 40 |
| Reaction temperature(° C.) | 75 | 70 | 65 | 60 | 55 | 65 | 80 | 70 |
| Reaction time(h) | 7 | 8 | 10 | 12 | 15 | 4 | 5 | 6 |
| Quality; yield(%) of product | 3.054 g; 81.1 | 2.941 g; 78.1 | 3.10 g; 82.3 | 3.024 g; 80.3 | 3.058 g; 81.2 | 1.883 g; 50.0 | 1.597 g; 42.4 | 1.168 g; 31.0 |

Example 3

Preparation of Ceritinib (Compound of Formula I)

Method One

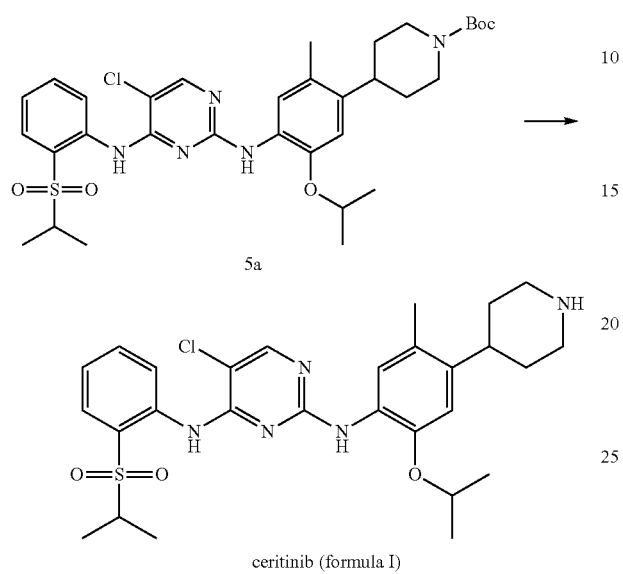

To a flask were added compound of formula 5a (200 g, 0.305 mol) and THF (1000 mL). The mixture was controlled at 0° C. to 5° C. when TFA (70 g, 0.61 mol) was slowly added. After the TFA dropwise addition, the mixture was kept at 20° C. to 25° C. and stirred for 6 hours. After the reaction, the reaction mixture was concentrated, then was quenched with saturated aqueous sodium bicarbonate (2000 mL) and separated with dichloromethane ($CH_2Cl_2$) (500 mL×3). The organic layer was washed with saturated aqueous sodium bicarbonate (1000 mL), and water (500 mL) and saturated aqueous sodium chloride (500 mL), dried over anhydrous sodium sulfate and filtered, and concentrated to obtain the raw product of ceritinib. To the raw product was added i-propanol (IPA) (480 mL). The mixture was heated until dissolved completely, cooled to 30° C., and then kept at 30° C., stirred and crystallized for 3 hours. The resulting mixture was filtered. The filter cake was dried in vacuo at 60° C. for 8 hours to obtain the ceritinib product (compound of formula I) as a white solid (149.9 g, 88.5%), HPLC purity:99.2%.

Example 4

Preparation of Ceritinib (Compound of Formula I)

Method One

Ceritinib may be prepared under the reaction conditions shown in table 2 according to the procedure described in Example 3.

TABLE 2

The reaction conditions for preparation of compound I

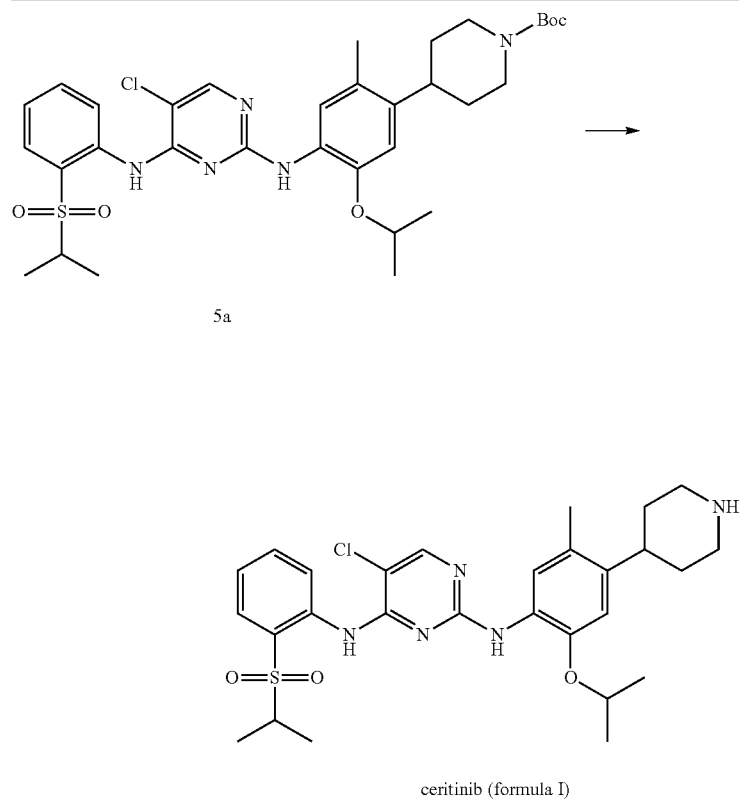

TABLE 2-continued

The reaction conditions for preparation of compound I

| | \multicolumn{5}{c}{No.} |
|---|---|---|---|---|---|
| | 1 | 2 | 3 | 4 | 5 |
| The mole ratio of (5a):(TFA); (the amount of compound 5a is 200 g) | 1:1.0 | 1:1.05 | 1:1.1 | 1:1.2 | 1:1.3 |
| Reaction solvent | THF | THF | THF | THF | THF |
| The mass/volume ratio of compound 5a/reaction solvent | 5 | 5 | 5 | 5 | 5 |
| TFA dropwise temperature (° C.) | −15 | −10 | −5 | 0 | 5 |
| Reaction temperature (° C.) | 10 | 15 | 20 | 22 | 25 |
| Reaction time (h) | 12 | 10 | 8 | 5 | 2 |
| Cooling temperature (° C.) | 25 | 20 | 15 | 30 | 10 |
| Recrystallization solvent | i-propanol | i-propanol | i-propanol | i-propanol | ethanol |
| The mass ratio of recrystallization solvent to compound I | 2 | 1.5 | 4 | 3 | 2.5 |
| Crystallization temperature (° C.) | 30 | 25 | 30 | 25 | −30 |
| Crystallization time (h) | 10 | 5 | 8 | 4 | 2 |
| Quality; | 151.3 g; | 148.4 g; | 149.6 g; | 152.8 g; | 148.2 g; |
| yield (%) of product | 89.2 | 87.5 | 88.2 | 90.1 | 87.4 |
| HPLC purity(%) | 98.9 | 99.6 | 99.0 | 98.8 | 99.5 |

| | \multicolumn{5}{c}{No.} |
|---|---|---|---|---|---|
| | 6 | 7 | 8 | 9 | 10 |
| The mole ratio of (5a):(TFA); (the amount of compound 5a is 200 g) | 1:1.5 | 1:1.8 | 1:2.0 | 1:2.5 | 1:2.2 |
| Reaction solvent | THF | THF | THF | THF | THF |
| The mass/volume ratio of compound 5a/reaction solvent | 5 | 5 | 5 | 5 | 5 |
| TFA dropwise temperature (° C.) | 8 | 10 | 15 | 5 | 0 |
| Reaction temperature (° C.) | 30 | 40 | 20 | 25 | 15 |
| Reaction time (h) | 1 | 0.5 | 3 | 4 | 6 |
| Cooling temperature (° C.) | 30 | 20 | 25 | 30 | 20 |
| Recrystallization solvent | n-propanol | i-propanol | i-propanol | i-propanol | i-propanol |
| The mass ratio of recrystallization solvent to compound I | 3 | 3.5 | 4 | 3 | 2.5 |
| Crystallization temperature (° C.) | −10 | −20 | −20 | 0 | 25 |
| Crystallization time (h) | 8 | 6 | 6 | 6 | 6 |
| Quality; | 149.8 g; | 151.1 g; | 152.3 g; | 151.3 g; | 150.1 g; |
| yield(%) of product | 88.3 | 89.1 | 89.8 | 89.2 | 88.5 |
| HPLC purity(%) | 99.2 | 99.8 | 99.0 | 98.9 | 99.5 |

Example 5

Preparation of Compound of Formula 5b

Method Two

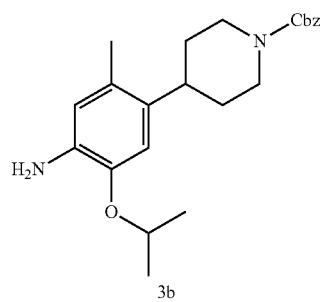

3b

+

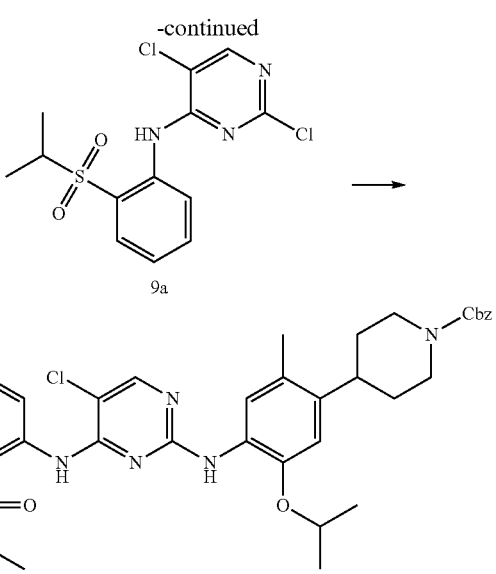

2,5-dichloro-N-(2-(isopropylsulfonyl)phenyl)pyrimidin-4-amine (compound of formula 9a, 2.0 g, 5.78 mmol) was dissolved in isopropanol (60.0 g), then added benzyl 4-(4- amino-5-isopropoxy-2-methylphenyl)piperidine-1-carboxylate (compound of formula 3b, 2.21 g, 5.78 mmol) and p-toluenesulfonic acid (0.995 g, 5.78 mmol). The mixture was stirred for 5 hours under 75° C., the reaction was finished by TLC test. After the reaction, the reaction mixture was concentrated under reduced pressure, the solid residues was dispersed with 200 mL ethyl acetate (EA). The organic layer was washed with saturated aqueous sodium bicarbonate (200 mL), water (100 mL) and saturated aqueous sodium chloride (100 mL), dried over anhydrous sodium sulfate and concentrated to give the compound of formula 5b product as a yellow powder (3.26 g, yield 81.6%).

Example 6

Preparation of Compound 5b

Method Two

The compound 5b may be prepared under the reaction conditions shown in table 3 according to the procedure described in Example 5.

TABLE 3

The reaction conditions for preparation of compound 5b

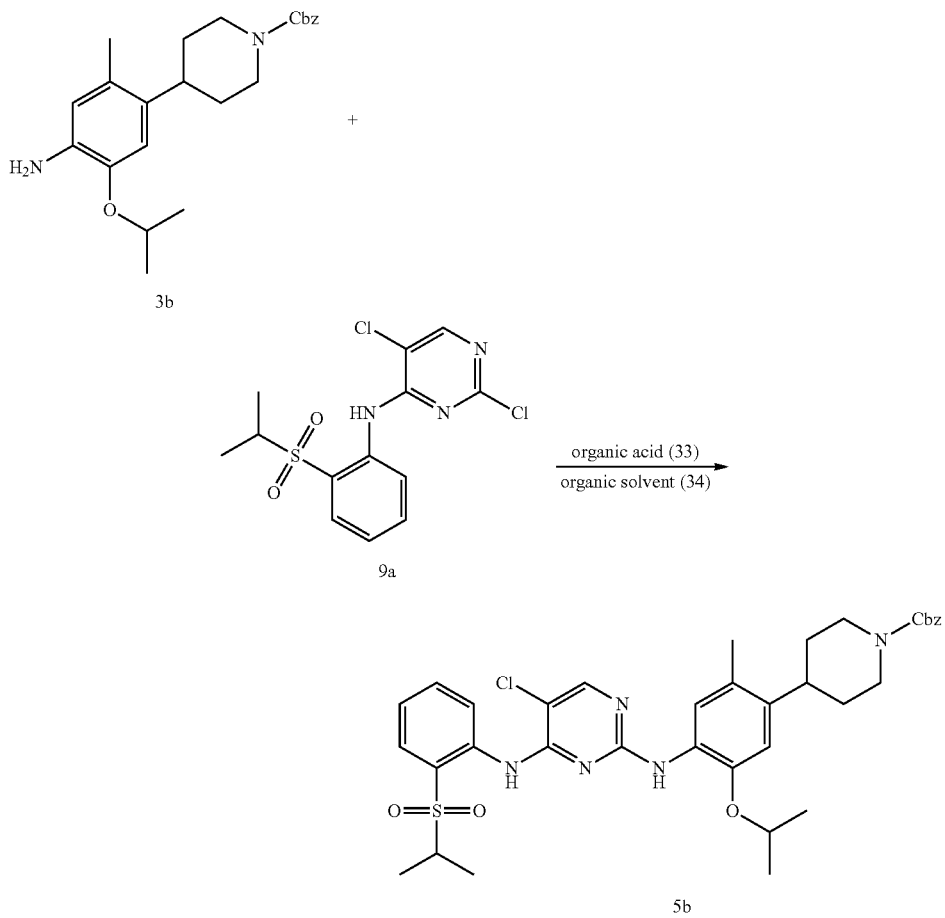

| | No. | | | | | | | |
|---|---|---|---|---|---|---|---|---|
| | 1 | 2 | 3 | 4 | 5 | 6 | 7 | 8 |
| The mole ratio of (3b):(9a):(33); (the amount of compound 3b is 2.21 g) | 1:0.98:0.95 | 1:1.1:1.35 | 1:1.25:1.1 | 1:1.0:1.3 | 1:0.95:1.4 | 1:1.15:1.2 | 1:1.2:1.15 | 1:1.05:1.25 |
| organic acid(33) | p-toluene sulfonic acid | p-toluene sulfonic acid | p-toluene sulfonic acid | p-toluene sulfonic acid | p-toluene sulfonic acid | p-toluene sulfonic acid | p-toluene sulfonic acid | p-toluene sulfonic acid |
| Reaction organic solvent(34) | IPA | IPA | IPA | IPA | IPA | IPA | IPA | IPA |
| The mass ratio of reaction solvent to compound 3b | 50 | 40 | 4 | 10 | 80 | 2 | 30 | 24 |

TABLE 3-continued

| The reaction conditions for preparation of compound 5b | | | | | | | | |
|---|---|---|---|---|---|---|---|---|
| Reaction temperature(° C.) | 90 | 85 | 80 | 85 | 75 | 75 | 85 | 78 |
| Reaction time(h) | 0.25 | 1 | 1.5 | 2 | 3 | 4 | 5 | 6 |
| Quality; yield(%) of product | 3.26 g; 81.5 | 3.19 g; 79.8 | 3.16 g; 79.0 | 3.22 g; 80.5 | 3.28 g; 82.0 | 3.16 g; 79.2 | 3.19 g; 79.9 | 3.24 g; 81.2 |

| | No. | | | | | | | |
|---|---|---|---|---|---|---|---|---|
| | 9 | 10 | 11 | 12 | 13 | 14 | 15 | 16 |
| The mole ratio of (3b):(9a):(33); (the amount of compound 3b is 2.21 g) | 1:1.4:0.98 | 1:1.05:12. | 1:1.3:1.05 | 1:1:1.1 | 1:1.35:1.0 | 1:0.95:1.5 | 1:1.5:0.95 | 1:1.1:1.0 |
| organic acid(33) | p-toluene sulfonic acid | p-toluene sulfonic acid | p-toluene sulfonic acid | p-toluene sulfonic acid | p-toluene sulfonic acid | p-toluene sulfonic acid | p-toluene sulfonic acid | p-toluene sulfonic acid |
| Reaction organic solvent(34) | IPA | IPA | IPA | IPA | IPA | ethanol | t-butanol | ethanol and water(v/v = 50:50) |
| The mass ratio of reaction solvent to compound 3b | 30 | 3 | 8 | 60 | 18 | 30 | 20 | 40 |
| Reaction temperature(° C.) | 75 | 70 | 65 | 60 | 55 | 65 | 80 | 70 |
| Reaction time(h) | 7 | 8 | 10 | 12 | 15 | 4 | 5 | 6 |
| Quality; yield(%) of product | 3.20 g; 80.1 | 3.16 g; 79.1 | 3.28 g; 82.0 | 3.23 g; 80.8 | 3.25 g; 81.4 | 1.40 g; 35.0 | 1.82 g; 45.6 | 1.54 g; 38.5 |

Example 7

Preparation of Ceritinib (Compound of Formula I)

Method Two

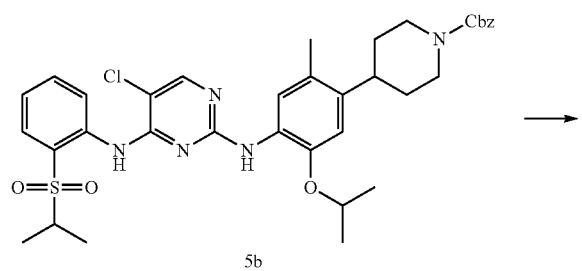

5b

→

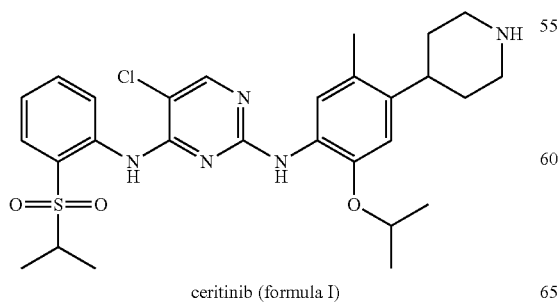

ceritinib (formula I)

To a flask were added compound of formula 5b (200 g, 0.289 mol) and THF (1000 mL). The mixture was controlled at 0° C. to 5° C. when TFA (51.3 g, 0.45 mol) was slowly added. After the TFA dropwise addition, the mixture was kept at 20° C. to 25° C. and stirred for 5 hours. After the reaction, the reaction mixture was concentrated, then was quenched with saturated aqueous sodium bicarbonate (2000 mL) and separated with dichloromethane ($CH_2Cl_2$) (500 mL×3). The organic layer was washed with saturated aqueous sodium bicarbonate (1000 mL), and water (500 mL) and saturated aqueous sodium chloride (500 mL), dried over anhydrous sodium sulfate and filtered, and concentrated to obtain the raw product of ceritinib. To the raw product was added i-propanol (IPA) (480 mL). The mixture was heated until dissolved completely, cooled to 30° C., and then kept at 30° C., stirred and crystallized for 4 hours. The resulting mixture was filtered. The filter cake was dried in vacuo at 60° C. for 8 hours to obtain ceritinib as a white powder (145.1 g, 90.0%), HPLC purity: 99.5%.

Example 8

Preparation of Ceritinib

Method Two

Ceritinib may be prepared under the reaction conditions shown in table 4 according to the procedure described in Example 7.

TABLE 4

The reaction conditions for preparation of ceritinib

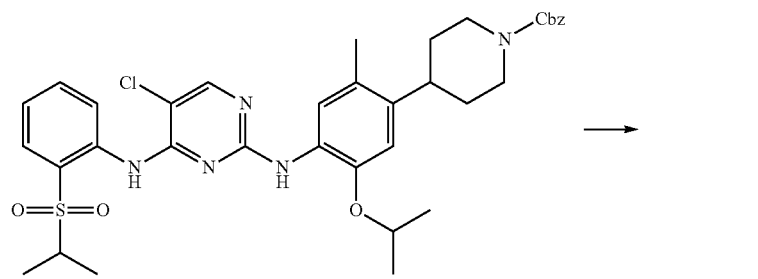

5b

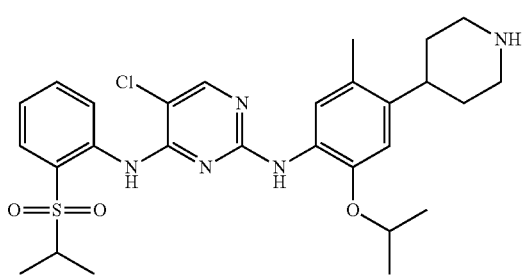

ceritinib (formula I)

| | No. | | | | |
|---|---|---|---|---|---|
| | 1 | 2 | 3 | 4 | 5 |
| The mole ratio of (5b):(TFA); (the amount of compound 5b is 200 g) | 1:1.0 | 1:1.05 | 1:1.1 | 1:1.2 | 1:1.3 |
| Reaction solvent | THF | THF | THF | THF | THF |
| The mass/volume ratio of compound 5b/reaction solvent | 5 | 5 | 5 | 5 | 5 |
| TFA dropwisetemperature (° C.) | −15 | −10 | −5 | 0 | 5 |
| Reaction temperature (° C.) | 10 | 15 | 20 | 22 | 25 |
| Reaction time (h) | 12 | 10 | 8 | 5 | 2 |
| Cooling temperature (° C.) | 25 | 20 | 15 | 30 | 10 |
| Recrystallization solvent | i-propanol | methanol | i-propanol | i-propanol | ethanol |
| The mass ratio of recrystallization solvent to ceritinib | 2 | 1.5 | 4 | 3 | 2.5 |
| Crystallization temperature (° C.) | 30 | 25 | 30 | 25 | −30 |
| Crystallization time (h) | 10 | 5 | 8 | 4 | 2 |
| Quality; yield(%) of product | 144.3 g; 89.5 | 142.8 g; 88.6 | 140.6 g; 87.2 | 145.3 g; 90.1 | 144.1 g; 89.4 |
| HPLC purity(%) | 99.5 | 99.0 | 98.8 | 98.9 | 99.1 |

| | No. | | | | |
|---|---|---|---|---|---|
| | 6 | 7 | 8 | 9 | 10 |
| The mole ratio of (5b):(TFA); (the amount of compound 5b is 200 g) | 1:1.5 | 1:1.8 | 1:2.0 | 1:2.5 | 1:2.2 |
| Reaction solvent | THF | THF | THF | THF | THF |
| The mass/volume ratio of compound 5b/reaction solvent | 5 | 5 | 5 | 5 | 5 |
| TFA dropwisetemperature (° C.) | 8 | 10 | 15 | 5 | 0 |
| Reaction temperature (° C.) | 30 | 40 | 20 | 25 | 15 |
| Reaction time (h) | 1 | 0.5 | 3 | 4 | 6 |
| Cooling temperature (° C.) | 30 | 20 | 25 | 30 | 20 |
| Recrystallization solvent | n-propanol | n-butanol | i-butanol | i-propanol | ethanol and water(v/v = 50:50) |
| The mass ratio of recrystallization solvent to ceritinib | 3 | 3.5 | 4 | 3 | 2.5 |
| Crystallization temperature (° C.) | −10 | −20 | −20 | 0 | 25 |
| Crystallization time (h) | 8 | 6 | 6 | 6 | 6 |
| Quality; | 147.2 g; | 144.1 g; | 144.8 g; | 145.4 g; | 144.3 g; |

TABLE 4-continued

| The reaction conditions for preparation of ceritinib | | | | | |
|---|---|---|---|---|---|
| yield(%) of product | 91.3 | 89.4 | 89.8 | 90.2 | 89.5 |
| HPLC purity(%) | 99.6 | 99.3 | 99.4 | 99.9 | 99.1 |

In the specification, unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications may be made in the embodiments without departing from spirit, principles and scope of the present disclosure.

What is claimed is:

1. A method for preparing ceritinib of formula I, comprising:

(1) contacting a compound of formula 12b with an amino protective group to obtain a compound of formula 3;

(2) contacting the compound of formula 3 with a compound of formula 9a to obtain a compound of formula 5; and (3) subjecting the compound of formula 5 to a deprotection reaction to obtain the ceritinib of formula I

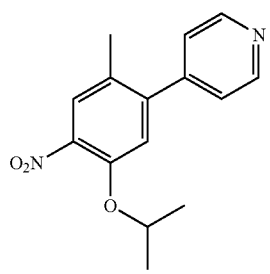

12b

-continued

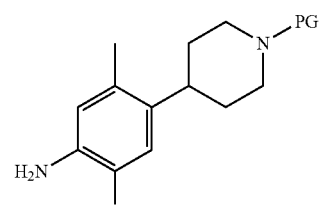

3

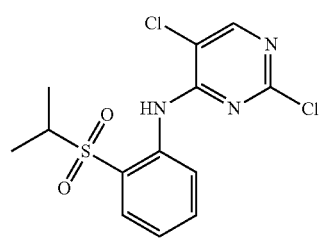

9a

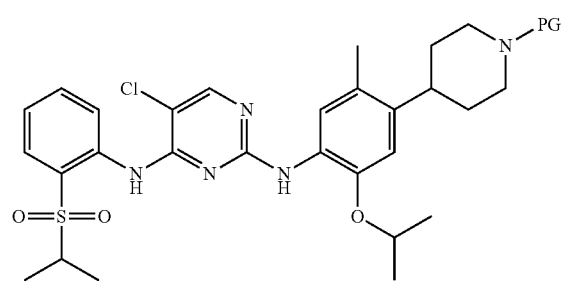

5

(formula I)

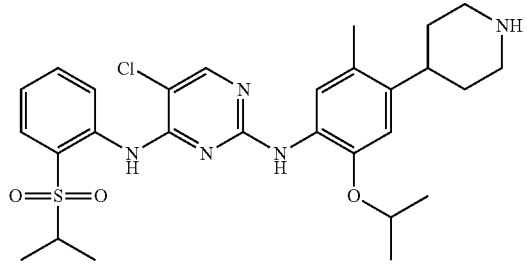

ceritinib with PG representing an amino protective group,
wherein the amino protective group is di-tert-butyl dicarbonate or benzyl chloroformate.

2. The method of claim 1, wherein the compound of formula 3 is contacted with the compound of formula 9a in presence of a Lewis acid or an organic acid.

3. The method of claim 2, wherein the compound of formula 3 is contacted with the compound of formula 9a under a temperature ranging about 50° C. to about 90° C.

4. The method of claim 3, wherein the compound of formula 3 is contacted with the compound of formula 9a with stirring for about 0.25 hour to about 15 hours.

5. The method of claim 4, wherein the amount of the compound of formula 9a is 0.95 equivalent to 1.50 equivalents per 1 equivalent by mole of the compound of formula 3a.

6. The method of claim 2, wherein the Lewis acid being $BF_3$, $SbF_5$, $AlCl_3$, $ZnCl_2$, and the organic acid being p-toluenesulfonic acid.

7. The method of claim 4, wherein the amount of Lewis acid is 0.95 equivalent to 1.50 equivalents per 1 equivalent by mole of the compound of formula 3a.

8. The method of claim 4, wherein, the organic solvent is IPA, and the amount of IPA is 2 equivalents to 80 equivalents per 1 equivalent by weight of the compound of formula 3a.

9. The method of claim 4, wherein step (2) comprises:
   dissolving the compound of formula 9a, 2.0 g, 5.78 mmol in isopropanol 60.0 g, and adding the compound of formula 3a, 2.0 g, 5.74 mmol and $AlCl_3$ 0.786 g, 5.76 mmol to the resulting mixture; and
   stirring the mixture for 6 hours under 80° C.

10. The method of claim 1, wherein the deprotection reaction is performed by contacting the compound of formula 5a with trifluoroacetic acid.

11. The method of claim 10, wherein the contacting of the compound of formula 5a with trifluoroacetic acid is performed under a temperature of about −15° C. to about 15° C.

12. The method of claim 10, wherein the amount of trifluoroacetic acid is 1.0 equivalent to 2.5 equivalents per 1 equivalent by mole of the formula 5a.

13. The method of claim 1, wherein in the step (1), the amino protective group is di-tert-butyl dicarbonate, and the step (3) comprises:
   (3-1) adding the compound of formula 5a (200 g, 0.305 mol and THF 1000 mL to a flask, slowly adding TFA to the resulting mixture with controlling the temperature of the mixture at 0° C. to 5° C., maintaining the temperature of the mixture at 20° C. to 25° C. and stirring the mixture for 6 hours, to form the compound of formula I;
   (3-2) concentrating the resulting reaction mixture, and quenching the reaction mixture with saturated aqueous sodium bicarbonate (2000 mL), separating the compound of formula I with 500 mL dichloromethane for three times, and washing the resulting organic layer with saturated aqueous sodium bicarbonate 1000 mL, water 500 mL and saturated aqueous sodium chloride 500 mL, drying and filtering the organic layer over anhydrous sodium sulfate, concentrating the resulting material to obtain a raw product of ceritinib;
   (3-3) adding i-propanol 480 mL to the raw product, and heating the resulting mixture until dissolved completely, cooling the mixture to 30° C., maintaining the temperature of the mixture at 30° C. with stirring and allowing the crystallization for 3 hours, and filtering the resulting mixture and drying the resulting filter cake in vacuo at 60° C. for 8 hours to obtain the ceritinib product as a white solid.

14. The method of claim 1, wherein in the step (1), the amino protective group is benzyl chloroformate, and the step (3) comprises:
   (3-a) adding the compound of formula 5b 200 g, 0.289 mol and THF 1000 mL to a flask, adding TFA 51.3 g, 0.45 mol slowly to the resulting mixture with controlling the temperature of the mixture, maintaining the temperature of the mixture at 20° C. to 25° C. and stirring the mixture for 5 hours, to form the compound of formula I;
   (3-b) concentrating the resulting reaction mixture, and quenching the reaction mixture with saturated aqueous sodium bicarbonate (2000 mL), separating the compound of formula I with 500 mL dichloromethane for three times, and washing the resulting organic layer with saturated aqueous sodium bicarbonate 1000 mL, water 500 mL and saturated aqueous sodium chloride 500 mL, drying and filtering the organic layer over anhydrous sodium sulfate, concentrating the resulting material to obtain a raw product of ceritinib; and
   (3-c) adding i-propanol 480 mL to the raw product, and heating the resulting mixture until dissolved completely, cooling the mixture to 30° C., maintaining the temperature of the mixture at 30° C. with stirring and allowing the crystallization for 3 hours, and filtering the resulting mixture and drying the resulting filter cake in vacuo at 60° C. for 8 hours to obtain the ceritinib product as a white solid.

* * * * *